United States Patent [19]

Steglich et al.

[11] 4,264,771

[45] Apr. 28, 1981

[54] ALKYLATION OF SUBSTITUTED OXAZOLINONE-(5) COMPOUNDS

[75] Inventors: Wolfgang Steglich, Berlin; Rudolf Hurnaus; Peter Gruber, both of Biberach; Boerries Kuebel, Berlin, all of Fed. Rep. of Germany

[73] Assignee: BASF Aktiengesellschaft, Fed. Rep. of Germany

[21] Appl. No.: 891,456

[22] Filed: Mar. 29, 1978

Related U.S. Application Data

[63] Continuation of Ser. No. 489,068, Jul. 16, 1974, abandoned.

[30] Foreign Application Priority Data

Jul. 19, 1973 [DE] Fed. Rep. of Germany ....... 2336718

[51] Int. Cl.$^3$ ............................................. C07D 265/10
[52] U.S. Cl. ................................... 548/228; 562/433; 562/441; 562/442; 562/443; 562/444; 562/445; 562/446; 562/553; 562/567; 562/568; 562/571; 562/575
[58] Field of Search .................. 260/307 A; 548/232, 548/228

*Primary Examiner*—Donald G. Daus
*Assistant Examiner*—D. B. Springer
*Attorney, Agent, or Firm*—Keil & Witherspoon

[57] ABSTRACT

Manufacture of 4-substituted oxazolinone-(5) compounds, which are intermediates for α-substituted aminoacids, by alkylation of 2-substituted or 3,4-disubstituted oxozolinone-(5) compounds in an aprotic solvent in the presence of a tertiary amine.

3 Claims, No Drawings

ALKYLATION OF SUBSTITUTED OXAZOLINONE-(5) COMPOUNDS

This is a continuation, of application Ser. No. 489,068 filed July 16, 1974, now abandoned.

This invention relates to a process for the production of 4-substituted oxazolinone-(5) compounds.

We have discovered a process for the manufacture of 4-substituted oxazolinone-(5) compounds, wherein 2-substituted oxazolinone-(5) compounds, which may already have a substituent in the 4-position, are substituted in the 4-position by reaction with an alkylating agent in an aprotic solvent in the presence of a tertiary amine, and the resulting oxazolinone-(5) compound is optionally hydrolyzed to the aminoacid.

The starting materials are oxazolinone-(5) compounds of the general formula I

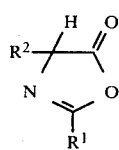

in which $R^1$ is hydrogen, an unsubstituted or substituted aromatic radical, straight-chain or branched-chain unsubstituted or substituted alkyl of 1 to 20, preferably 1 to 10, carbon atoms, or a cycloaliphatic radical of 5 to 8 ring members.

The preferred aromatic radical $R^1$ is phenyl which can be substituted, for example by halogen, nitro, alkoxy or lower alkyl, especially methyl or ethyl.

Examples of substituted phenyl are chlorophenyl, bromophenyl, nitrophenyl, methoxyphenyl, dimethoxyphenyl, tolyl and ethylphenyl.

Examples of suitable alkyl $R^1$ are methyl, ethyl, propyl, i-propyl-butyl, i-butyl, sec.-butyl, tert.-butyl, n-pentyl, heptyl, octyl, decyl and dodecyl.

Examples of substituents of the alkyl radicals are amino groups which carry an acyl radical as a substituent of the nitrogen, such as 1-benzamino-isobutyl, 1-benzamino-2-phenyl-ethyl, benzaminomethyl, 1-benzamino-ethyl and the corresponding acetamino radicals. Further substituents of the alkyl radicals are ester groups, nitrile and aryl radicals, especially phenyl radicals, such as benzyl or β-phenyl-ethyl.

Examples of cycloaliphatic radicals are cyclopentyl, cyclohexyl and cycloheptyl.

The preferred starting compounds are 2-phenyl-oxazolinone-(5) compounds which already have a substituent in the 4-position, so that 4,4-disubstituted oxazolinone compounds are produced by the process of the invention.

$R^2$ is hydrogen, straight-chain or branched-chain alkyl of 1 to 20 carbon atoms, which can be substituted, unsubstituted or substituted aryl or cycloalkyl of 5 to 8 ring members.

Individual examples of $R^2$ are: as alky-methyl, ethyl, propyl, isopropyl, butyl, isobutyl, sec.-butyl, pentyl, heptyl, octyl, decyl, dodecyl and pentadecyl; as substituted alkyl-in particular, alkyl substituted by phenyl which may be additionally substituted in the aromatic ring, such as benzyl, β-phenylethyl, β-phenylpropyl, methoxybenzyl, dimethoxybenzyl, acetoxybenzyl, diacetoxybenzyl, methylenedioxybenzyl and p-chlorobenzyl.

Further possible substituents of the alkyl radicals are alkoxy, alkylthio, acylamino and carbethoxy radicals, such as methoxymethyl, β-methylthioethyl, γ-acetylaminopropyl, γ-benzaminopropyl, δ-acetylaminobutyl, δ-benzaminobutyl, carbethoxymethyl, carbethoxyethyl, β-carbethoxymethyl and β-carbethoxy ethyl.

Examples of aryl $R^2$ are phenyl, p-chlorophenyl, methoxyphenyl, dimethoxyphenyl, acetoxyphenyl and nitrophenyl.

Examples of cycloalkyl $R^2$ are cyclopentyl, cyclohexyl, cycloheptyl and cyclooctyl.

The compounds of the formula I to be used as starting materials can be obtained by conventional methods, for example as described in the publications by H.E. Carter, Organic Reactions, Vol. III, page 198 (1949), or J.W. Cornforth, "The Chemistry of Penicillin", edited by H.T. Clarke, J.R. Johnson and R. Robinson, Princeton University Press (1949), pages 730 et seq.

Alkylating agents are compounds by means of which alkyl or substituted alkyl radicals can be introduced into compounds of the formula I.

Examples of alkylating agents are therefore alkyl halides, in particular alkyl bromides and alkyl iodides of 1 to 10 carbon atoms, such as methyl, ethyl, propyl, butyl, and isobutyl bromides and iodides and 2-ethylhexyl bromide. The alkyl halides can contain double bonds and triple bonds. Allyl halides, such as allyl bromide or prenyl chloride and propargyl halides, such as propargyl bromide or geranyl bromide, are preferred.

In turn, the alkyl radicals can carry substituents and accordingly the following can be used as alkylating agents: benzyl halides, for example benzyl chloride, benzyl bromide, nitrobenzyl chloride, dimethoxybenzyl chloride, p-chlorobenzyl bromide, methoxybenzyl chloride, 3,4-methylenedioxybenzyl chloride, acetoxybenzyl chloride, p-methylbenzyl chloride, 2,4-dimethylbenzyl chloride, 3,4-dimethylbenzyl chloride, trityl chloride or trityl fluoborate, halomethyl ketones, such as phenacyl bromide and chloroacetone, chloroacetic acid or chloroacetic acid esters, for example ethyl chloroacetate.

Tropylium perchlorate is a further example of a possible alkylating agent.

As a rule, the reaction of a starting material with the alkylating agent is carried out with equimolar amounts in an anhydrous aprotic solvent in the presence of a tertiary amine as the base. However, one of the compounds to be reacted can also be used in excess.

Examples of suitable solvents to use are chlorinated aliphatic hydrocarbons, such as methylene chloride or chloroform, aromatic hydrocarbons, such as benzene or toluene, amides of lower aliphatic carboxylic acids, in particular dimethylformamide or hexamethylphosphoric acid triamide, or dimethylsulfoxide, or mixtures of the said solvents.

A solvent of low polarity, such as benzene, methylene chloride or tetrahydrofuran, is appropriate for very reactive alkylating agents, such as, for example, trityl chloride, tropylium perchlorate or phenacyl chloride; for alkylation with alkyl halides, the use of dipolar aprotic solvents, such as dimethylformamide, dimethylsulfoxide or hexamethylphosphoric acid triamide is preferred.

Examples of suitable tertiary amines to use, which are in general employed in excess, are triethylamine, ethyldiisopropylamine, so-called Hünig's bases (Hünig and Kiessel, Chem. Ber., 91,308 (1958) N,N-dimethylcyclohexylamine, pyridine or picolines. Ethyldiisopropylamine has proved a particularly suitable base.

In general, the reactions are carried out at temperatures from 0° C. to room temperature or at elevated temperatures, suitably up to 100° C. At times it can also be appropriate to carry out the reaction at temperatures below 0° C., for example at −10° C. or below.

In some cases, for example when using benzyl chloride or ethyl chloroacetate as alkylating agents, the addition of potassium iodide assists the alkylation.

Working up the resulting 4-substituted oxazolinone compounds presents no difficulties and is carried out by conventional methods, for example by adding water and extracting by shaking with a water-insoluble organic solvent.

It is surprising that under the reaction conditions according to the invention the 4-substituted and 4,4-disubstituted oxazolinone derivatives can be manufactured from optionally 2-substituted oxazolinone-(5) compounds without difficulties and in good to very good yields, whilst from the known state of the art, for example as with acylations, enolethers or mixtures with the corresponding enolethers would have been expected.

The following oxazolinone-(5) compounds may be mentioned in addition to the compounds indicated in the Examples: 4-(β-carbethoxyethyl)-4-cycloheptatrienyl-2-phenyl-oxazolinone-(5) (from I, $R^1=C_6H_5$, $R^2=CH_2CH_2CO_2C_2H_5$ and tropylium perchlorate); 4-(β-carbethoxyethyl)-4-phenacyl-2-phenyl-oxazolinone-(5) (from I, $R^1=C_6H_5$, $R^2=CH_2CH_2CO_2C_2H_5$ and phenacyl bromide); 4-ethyl-4-(δ-acetaminobutyl)-2-phenyl-oxazolinone-(5) from I, $R^1=C_6H_5$, $R^2=(CH_2)_4NHCOCH_3$ and ethyl iodide); 4-(3,3-dimethylallyl)-4-(γ-benzaminopropyl)-2-phenyl-oxazolinone-(5) (from I, $R^1=C_6H_5$, $R^2=(CH_2)_3NHCOCH_3$ and 3,3-dimethylallyl bromide); 4-propyl-4-(γ-acetaminopropyl)-2-phenyl-oxazolinone-(5) (from I, $R^1=C_6H_5$, $R^2=(CH_2)_3NHCOCH_3$ and propyl iodide).

The substituted oxazolinones prepared in accordance with the invention are excellent starting materials for the manufacture of aminoacids, preferably of α-substituted amino-acids. For example, α-alkyl derivatives of the aminoacids glycine, alanine and leucine and the corresponding noraminoacids, phenylalanine, protected derivatives of tyrosine, dopa, lysine, ornithine, arginine, histidine, tryptophan and half-esters of aspartic and glutamic acid can be manufactured.

For this purpose, the oxazolinones can be used as pure substances or in the form resulting from the alkylation according to the invention, without undergoing purification.

The hydrolysis to the aminoacid is as a rule carried out under said conditions, by conventional methods. For this purpose, a mixture of glacial acetic acid and concentrated aqueous hydrochloric acid is used with advantage.

It is of interest that the hydrolysis of 4-(propin-(2)-yl)-2-phenyl-4-isopropyl-oxazolinone-(5) gives the levulinic acid derivative of the formula

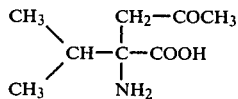

Further examples of aminoacids are α-phenacetylglutamic acid, α-ethyl-lysine, α-propyl-ornithine and α-(o-nitrobenzyl)-ornithine.

EXAMPLE 1

4-allyl-2-phenyl-4-benzyl-oxazolinone-(5)

10 g (40 millimoles) of 2-phenyl-4-benzyl-oxazolinone-(5) and 4.9 g (40 millimoles) of allyl bromide in 50 ml of absolute dimethylformamide are stirred with 6.75 g (51.5 millimoles) of ethyldiisopropylamine for 4 days at room temperature. 200 ml of water are then added and the mixture is extracted with five times 30 ml of methylene chloride. The combined extracts are extracted by shaking with 0.5N hydrochloric acid and with water and then dried over magnesium sulfate, and the solvent is evaporated off under reduced pressure. 4-allyl-2-phenyl- 4-benzyl-oxazolinone-(5) remains as a yellow analytically pure oil, in a yield of 10.8 g (93%).

$C_{19}H_{17}NO_2$ (291.4): found C 78.27; H 6.18; N 4.98; calculated C 78.36; H 5.88; N 4.81.

EXAMPLE 2

4-isopropyl-4-allyl-2-phenyl-oxazolinone-(5)

4 g of 4-isopropyl-2-phenyl-oxazolinone-(5) are stirred with 2.4 g of allyl bromide and 3.0 g of ethyldiisopropylamine in 20 ml of absolute dimethylformamide at room temperature for 3 days. Amine hydrobromide which precipitates is filtered off and the solution is mixed with 150 ml of water and then extracted with five times 30 ml of methylene chloride. The combined extracts are extracted by shaking with 0.5N hydrochloric acid and with water, and then dried over magnesium sulfate, and the solvent is distilled off under reduced pressure. 4.8 g of a yellowish liquid, representing 100% crude yield of 4-isopropyl-4-allyl-2-phenyl-oxazolinone-(5), remain. Distillation in a high vacuum gives 2.9 g (60%) of an almost colorless liquid of boiling point 98° C. at 0.1 mm Hg.

$C_{15}H_{17}NO_2$ (243.3): found C 74.12; H 7.08; N 5.76; calculated C 74.09; H 7.03; N 5.75.

EXAMPLE 3

4-isopropyl-4-benzyl-2-phenyl-oxazolinone-(5)

4.0 g of 4-isopropyl-2-phenyl-oxazolinone-(5), 3.0 g of ethyldiisopropylamine and 2.53 g of benzyl chloride are stirred in 20 ml of absolute dimethylformamide, with a little added potassium iodide, for 4 days at room temperature. The mixture is then diluted with 150 ml of water and extracted with five times 30 ml of methylene chloride. The combined extracts are shaken with 0.5N hydrochloric acid and with water, and then dried with magnesium sulfate, and the solvent is distilled off under reduced pressure. 4-isopropyl-2-phenyl-4-benzyl-oxazolinone-(5) remains as a pale yellow oil which is approx. 85% pure. Distillation gives 2.3 g (40%) yield.

EXAMPLE 4

4-isopropyl-2-phenyl-4-(2-nitrobenzyl)-oxazolinone-(5)

4.0 g of 4-isopropyl-2-phenyl-oxazolinone-(5), 3.0 g of ethyldiisopropylamine and 3.42 g of 2-nitrobenzyl chloride in 20 ml of absolute dimethylformamide are stirred for 3 days at room temperature. The mixture is then diluted with 150 ml of water and extracted with five times 30 ml of methylene chloride. The combined extracts are extracted by shaking with 0.5N hydrochloric acid and with water, and then dried with magnesium sulfate, and the solvent is distilled off under reduced pressure. The solid residue is recrystallized from ethyl acetate/petroleum ether. 6.6 g (66%) of 4-isopropyl-2-phenyl-4-(-2-nitrobenzyl)-oxazolinone-(5) are obtained as colorless crystals; the melting point is from 113° to 116° C., and 121° C. after a further recrystallization.

$C_{19}H_{18}N_2O_4$ (338.4): found C 67.26; H 5.57; N 8.28; calculated C 67.45; H 5.36; N 8.28.

EXAMPLE 5

4-isopropyl-2-phenyl-4-(2-oxo-phenylethyl)-oxazolinone-(5)

11.8 g of 4-isopropyl-2-phenyl-oxazolinone-(5) and 12 g of phenacyl bromide are dissolved in 20 ml of ethyldiisopropylamine and 5 ml of dimethylsulfoxide. The solution is then heated to 70° C. for 2.5. hours, in the course of which a thick white precipitate forms. The mixture is evaporated under reduced pressure, the residue is taken up in methylene chloride and the solution is washed with 0.1N hydrochloric acid and water, dried and again evaporated. The solid which remains is recrystallized from chloroform/hexane.

Yield: 12.5 g (67%) of 4-isopropyl-2-phenyl-4-(2-oxophenyl-ethyl)-oxazolinone-(5) of melting point 151° C. (from tetrahydrofuran).

$C_{20}H_{19}NO_3$ (321.4): found C 75.07; H 6.03; N 4.42; calculated C 74.75; H 5.96; N 4.36.

EXAMPLE 6

4-isopropyl-2-phenyl-4-cycloheptatrienyl-oxazolinone-(5)

4-isopropyl-2-phenyl-oxazolinone-(5) in methylene chloride is reacted with an equimolar amount of tropylium perchlorate and triethylamine for 12 hours at 0° C. The mixture is then extracted by shaking with 0.1N hydrochloric acid and dried with magnesium sulfate, and the solvent is distilled off under reduced pressure. This leaves 4-isopropyl-4-cycloheptatrienyl-2-phenyl-oxazolinone-(5) as a spectroscopically pure pale yellow oil, in over 90% yield.

EXAMPLE 7

4-isopropyl-2-[(1'-benzamino)-isobutyl]-4-cycloheptatrienyloxazolinone-(5)

The oxazolinone obtained from N-benzoyl-DL-Val-Val-CH by heating with a five-fold excess of acetic anhydride to 110° C. for 15 minutes is reacted, in methylene chloride, with equimolar amounts of triethylamine and tropylium perchlorate for 12 hours at 0° C. The mixture is then extracted by shaking with 0.1N hydrochloric acid and dried over magnesium sulfate, and the solvent is distilled off under reduced pressure. This leaves 4-isopropyl-2-[1'-benzamino)-isobutyl]-4-cycloheptatrienyl-oxazolinone-(5) as a spectroscopically pure, pale yellow oil in more than 90% yield.

EXAMPLE 8

2-phenyl-4-triphenylmethyl-oxazolinone-(5)

(a) 6.0 g of trityl chloride and 3.0 ml of α-picoline are dissolved in 30 ml of methylene chloride. A solution of 3.2 g of 2-phenyl-oxazolinone-(5) in 30 ml of methylene chloride is slowly added dropwise, whilst stirring. After stirring for 2 days, the violet solution is extracted by shaking with 40 m of 0.5N hydrochloric acid and dried with magnesium sulfate, and the solvent is distilled off under reduced pressure. The solid which remains is digested with ethyl acetate, filtered off and washed with ethyl acetate. This leaves 2.2 g (27%) of 2-phenyl-4-triphenylmethyloxazolinone-(5) as a colorless powder of melting point 183° C.; after recrystallization from benzene/ethyl acetate, the melting point is 192° C. (with decomposition).

$C_{28}H_{21}NO_2$ (403.5): found C 83.37; H 5.14; N 3.30; calculated C 83.35; H 5.24; N 3.47. (b) 13.0 g of trityl fluoborate are dissolved in 80 ml of methylene chloride, 6 ml of absolute α-picoline are added whilst cooling in a mixture of ice and common salt, and a solution of 4.8 g of 2-phenyl-oxazolinone-(5) in 60 ml of methylene chloride is then very slowly added dropwise at −10° C., whilst stirring. After 2 days, the mixture is extracted by shaking with 0.5N hydrochloric acid and then dried with magnesium sulfate, and the methylene chloride is removed whilst replacing it, in portions, by ethyl acetate. The precipitate formed is then filtered off and washed with ethyl acetate. 6.1 g (50%) of melting point 182° C. remain.

EXAMPLE 9

2-phenyl-4,4-bis-cycloheptatrienyl-oxazolinone-(5)

5 g of 2-phenyl-oxazolinone-(5), 5 g of tropylium perchlorate and 10 ml of triethylamine in 80 ml of benzene are stirred for 3 hours at room temperature. Ethyl acetate is added to the violet solution which is successively extracted by shaking with dilute hydrochloric acid and sodium bicarbonate solution, dried over sodium sulfate and evaporated. The oil residue is crystallized from methanol. 2-phenyl-4,4-bis-cycloheptatrienyl-oxazolinone-(5) crystallizes in yellow needles of melting point 109° to 111° C. The yield is 3.45 g (33%).

$C_{23}H_{19}NO_2$ (341.4): found C 80.35; H 5.72; N 3.99; calculated C 80.91; H 5.61; N 4.10;

EXAMPLE 10

4-methyl-2-phenyl-4-benzyl-oxazolinone-(5)

2.5 g of 2-phenyl-4-benzyl-oxazolinone-(5) and 2.4 g of methyl iodide in 10 ml of absolute dimethylformamide are stirred with 2.4 g of ethyldiisopropylamine for 5 hours at 90° C. The mixture is then diluted with 100 ml of water and extracted with five times 20 ml of methylene chloride. The combined extracts are extracted by shaking with 0.5N hydrochloric acid and with water and then dried with magnesium sulfate, and the solvent is evaporated off under reduced pressure. Distillation of the residue in a high vacuum gives a colorless oil of boiling point 113° to 115° C. at 0.07 mm Hg, in a yield of 0.9 g (34%).

$C_{17}H_{15}NO_2$ (265.3): found C 76.64; H 5.85; N 5.30; calculated C 77.00; H 5.70; N 5.28.

EXAMPLE 11

4-(4-isopropyl-2-phenyl-oxazolinon-(5)-yl)-acetic acid ethyl ester 4.0 g of 4-isopropyl-2-phenyl-oxazolinone-(5), 4.9 g of ethyl chloroacetate, 6.0 g of ethyldiisopropylamine and 1.0 g of potassium iodide in 20 ml of absolute dimethylformamide are stirred for 6 hours at 95° C. The mixture is then diluted with 20 ml of water and extracted with five times 30 ml of methylene chloride. The combined extracts are washed with 0.5N hydrochloric acid and with water and then dried with magnesium sulfate, and the solvent is evaporated off under reduced pressure. Distillation of the residue in a high vacuum gives a yellow oil of boiling point 130° C. at 0.15 mm Hg, in a yield of 4.35 g (75%).

$C_{16}H_{19}NO_4$ (289.3): found C 66.20; H 6.62; N 5.05; calculated C 66.43; H 6.62; N 4.84.

EXAMPLE 12

(a) 4-(2-phenyl-4-benzyl-oxazolinon-(5)-yl)-acetic acid ethyl ester 2.5 g of 2-phenyl-4-benzyl-oxazolinone-(5), 2.45 g of ethyl chloroacetate, 3.6 g of ethyldiisopropylamine and 0.5 g of potassium iodide in 10 ml of absolute dimethylformamide are stirred for 6 hours at 95° C. The mixture is then diluted with 100 ml of water and extracted with five times 20 ml of methylene chloride. The combined extracts are washed with 0.5N hydrochloric acid and with water and then dried with magnesium sulfate, and the solvent is evaporated off under reduced pressure. 2.9 g of a brown oil, which slowly crystallizes in the refrigerator, remain. Recrystallization from ether/petroleum ether gives 1.50 g (45%) of colorless crystals of melting point 80° C.

$C_{20}H_{19}NO_4$ (337.4): found C 71.13; H 5.84; N 4.23; calculated C 71.20; H 5.68; N 4.15. (b) 0.5 g of 4-(2-phenyl-oxazolinon-(5)-yl)-acetic acid ethyl ester, 0.26 g of benzyl chloride, 0.3 g of ethyldiisopropylamine and 0.1 g of potassium iodide in 5 ml of absolute dimethylformamide are stirred for 4 days at room temperature. Working up carried out as in Example 12(a) gives 0.6 g of yellow oil which matches the product obtained under 12(a).

EXAMPLE 13

4-ethyl-4-benzyl-2-phenyl-oxazolinone-(5)

2.5 g of 4-benzyl-2-phenyl-oxazolinone-(5), 3.0 g of ethyl iodide and 3.0 g of ethyldiisopropylamine in 10 ml of absolute dimethylformamide are stirred for 9 hours at 95° C. The mixture is then diluted with 100 ml of water and extracted with five times 20 ml of methylene chloride. The combined extracts are washed with 0.5N hydrochloric acid and with water, dried with magnesium sulfate, and freed from the solvent under reduced pressure. Distillation in a high vacuum gives 0.9 g (32%) of 4-ethyl-4-benzyl-2-phenyl-oxazolinone-(5) as a pale yellow oil of boiling point 127° C. (0.04 mm Hg). The compound is pure, according to the NMR spectrum.

EXAMPLE 14

2-benzyl-4-isopropyl-4-(propen-2-yl)-2-oxazolinone-(5)

2.6 g of 2-benzyl-4-isopropyl-2-oxazolinone-(5), 3.0 g of allyl bromide and 4.5 g of ethyldiisopropylamine in 15 ml of absolute dimethylformamide are stirred for 3 days at room temperature. The mixture is then diluted with 100 ml of water and extracted with five times 20 ml of methylene chloride. The combined extracts are washed with 0.5N hydrochloric acid and with water and then dried with magnesium sulfate, and the solvent is removed under reduced pressure. On distillation in a high vacuum, the red-yellow oil gives 2.0 g (65%) of 2-benzyl-4-isopropyl-4-(propen-2-yl)-2-oxazolinone-(5) as a colorless liquid, boiling point from 107° to 111° C. at 0.2 mm Hg.

EXAMPLE 15

4-(propin-(2)-yl)-2-phenyl-4-benzyl-oxazoline-(5)

2.5 g of 2-phenyl-4-benzyl-oxazolinone-(5), 2.4 g of propargyl bromide and 3.0 g of ethyldiisopropylamine in 10 ml of absolute dimethylformamide are stirred either (a) for 4 hours at 95° C. or (b) for 3 days at room temperature.

In both cases, the reaction solution is evaporated under reduced pressure, the residue is dissolved in 30 ml of methylene chloride and the solution is washed with 100 ml of 0.5N hydrochloric acid, 100 ml of sodium bicarbonate solution and 100 ml of water. It is then dried with magnesium sulfate and the solvent is evaporated off under reduced pressure. The oils which remain crystallize gradually. Recrystallization from ether/petroleum ether in each case gives 1.25 g (43%) of yellowish crystals of melting point 64° C.; after distillation in a high vacuum (boiling point 160° C. at 0.1 mm Hg), the product is analytically pure and almost colorless, and melts at 64° C.

$C_{19}H_{15}NO_2$ (289.2): found C 78.51; H 5.29; N 5.06; calculated C 78.90; H 5.22; N 4.84.

EXAMPLE 16

4-isopropyl-4-(propin-2-yl)-2-phenyl-oxazolinone-(5)

2.0 g of 4-isopropyl-2-phenyl-oxazolinone-(5), 2.4 g of propargyl bromide and 3.0 g of ethyldiisopropylamine in 10 ml of dimethylformamide are stirred for 3.5 days at room temperature. The mixture is then evaporated under reduced pressure, the residue is taken up in 50 ml of ethyl acetate, the solution is washed once with 100 ml of 0.5N hydrochloric acid, once with 100 ml of sodium bicarbonate solution and once with 100 ml of water and then dried with magnesium sulfate, and the solvent is evaporated off under reduced pressure. Distillation, in a high vacuum, of the oil which remains gives a colorless liquid, of boiling point from 103° to 104° C. at 0.25 mm Hg, in a yield of 1.75 g (72.5%).

$C_{15}H_{15}NO_2$ (241.3): found C 74.54; H 6.39; N 5.81; calculated C 74.66; H 6.26; N 5.81.

EXAMPLE 17

4-geranyl-4-isopropyl-2-phenyl-2-oxazolinone-(5)

2.0 g of 4-isopropyl-2-phenyl-2-oxazolinone-(5) in 10 ml of absolute dimethylformamide are mixed with 1.5 g of ethyldiisopropylamine. 2.17 g of geranyl bromide, dissolved in 10 ml of absolute dimethylformamide, are added dropwise in the course of 7 hours at room temperature, whilst stirring. After stirring for 3 days at room temperature, the mixture is worked up by pouring it into 200 ml of 0.5N hydrochloric acid and extracting with four times 30 ml of ether. The combined extracts are extracted by shaking with 150 ml of water, dried and freed from the solvent under reduced pressure. The analytically pure compound is left as a pale yellow oil, in a yield of 3.1 g (91%).

$C_{22}H_{29}NO_2$ (339.5) calculated C 77.84; H 8.61; N 4.13; found C 77.77; H 8.67; N 4.21.

Hydrolysis of 4-substituted oxazolinones-(5) to α-aminoacids

1. α-benzyl-valine from 4-isopropyl-2-phenyl-4-benzyl-oxazolinone-(5)

2.0 g of 4-isopropyl-2-phenyl-oxazolinone-(5), 1.9 g of benzyl chloride, 2.5 g of ethyldiisopropylamine and 0.5 g of potassium iodide in 10 ml of absolute dimethylformamide are stirred for 4 days at room temperature. The dimethylformamide is then distilled off under reduced pressure, the residue is taken up in 30 ml of methylene chloride, the solution is washed with 100 ml of 0.5N hydrochloric acid and 100 ml of water and then dried with magnesium sulfate and the solvent is evaporated off under reduced pressure. This leaves 2.8 g of a pale yellow liquid which according to the NMR spectrum consists of 85% of 4-isopropyl-2-phenyl-4-benzyl-oxazolinone-(5) and 15% of benzyl chloride.

This liquid is dissolved in 15 ml of glacial acetic acid and 10 ml of concentrated aqueous hydrochloric acid and the solution is stirred for 7 hours at 95° C. The solvent is then evaporated off under reduced pressure and the residue is taken up in a mixture of chloroform and water (in the ratio of 1:1). The aqueous phase is separated off, concentrated and neutralized with n-butylamine to a pH value of 7. It is then evaporated to dryness and the solid which remains is shaken with methanol, filtered off and rinsed with a little methanol.

The yield of α-benzyl-valine is 0.73 g, representing 35% based on 4-isopropyl-2-phenyl-oxazolinone-(5) employed. The product is a colorless powder which sublimes from 240° C. onward.

$C_{12}H_{17}NO_2$ (207.3)

Mass spectrum (high resolution): 208.135; $C_{12}H_{18}NO_2 = M + 1$

2. α-(2-nitrobenzyl)-valine from 4-isopropyl-2-phenyl-4-(2-nitrobenzyl)-oxazolinone-(5)

1.7 g of 4-isopropyl-2-phenyl-4-(2-nitrobenzyl)-oxazolinone-(5) in 15 ml of glacial acetic acid and 15 ml of concentrated hydrochloric acid are stirred for 6 hours at 95° C. The mixture is then evaporated under reduced pressure, the residue is taken up in 30 ml of water and the solution is extracted by shaking with tetrachloromethane. The aqueous phase is separated off and concentrated to approx. 10 ml under reduced pressure. It is then neutralized to pH 7 with sodium hydroxide and ultimately with sodium bicarbonate. A colorless precipitate results, which is filtered off and recrystallized from methanol. Yield: 0.9 g, corresponding to 72%; melting point 262° C. (with decomposition).

$C_{12}H_{16}N_2O_4$ (252.3): found C 56.95; H 6.62; N 11.12; calculated C 57.16; H 6.39; N 11.11.

3. α-(p-nitrobenzyl)-valine from 4-isopropyl-2-phenyl-oxazolinone-(5)

4.0 g of 4-isopropyl-2-phenyl-oxazolinone-(5) and 3.4 g of p-nitrobenzyl chloride in 20 ml of absolute dimethylformamide are stirred with 3.0 g of ethyldiisopropylamine and 0.3 g of potassium iodide for 3 days at room temperature. The mixture is then diluted with 200 ml of water and extracted with five times 30 ml of methylene chloride, and the combined organic phase is extracted by shaking with 0.5N hydrochloric acid and with water, then dried with magnesium sulfate and evaporated under reduced pressure. This leaves 6.0 g of a brown oil which according to the NMR spectrum contains 82% of 4-isopropyl-2-phenyl-4-p-nitrobenzyl)-oxazolinone-(5). This oil is dissolved in 30 ml of glacial acetic acid, 5 ml of concentrated hydrochloric acid are added and the mixture is stirred for 6½ hours at 95° C. It is then evaporated under reduced pressure, the residue is dissolved in a mixture of ethyl acetate and water (ratio 1:1), and the aqueous phase is separated off, concentrated to approx. 10 ml and neutralized to pH 7 with sodium bicarbonate. This produces a colorless precipitate which is filtered off and washed with water, acetone and ether. The yield is 2.2 g, representing 44% based on 4-isopropyl-2-phenyl-oxazolinone-(5); the product is a colorless powder which sublimes from approx. 270° C. onward.

$C_{12}H_{16}N_2O_4$ (252.2): found C 56.73; H 6.25; N 10.91; calculated C 57.15; H 6.39; N 11.11.

4. α-methyl-phenylalanine from 4-methyl-2-phenyl-4-benzyl-oxazolinone-(5)

2.5 g of 2-phenyl-4-benzyl-oxazolinone-(5) and 2.8 g of methyl iodide in 10 ml of absolute dimethylformamide are stirred with 3.0 g of ethyl diisopropylamine for 5 hours at 90° C. The mixture is then diluted with 100 ml of water and extracted with 5 times 20 ml of methylene chloride. The combined extracts are extracted by shaking with 100 ml of 0.5N hydrochloric acid and with 100 ml of water and then dried with magnesium sulfate, and the solvent is distilled off under reduced pressure. This leaves 2.6 g of a yellow oil which according to the NMR spectrum contains 75% of 4-methyl-2-phenyl-4-benzyl-oxazolinone-(5).

This oil is dissolved in 20 ml of glacial acetic acid, 10 ml of concentrated hydrochloric acid are added and the mixture is stirred for 5 hours at 95° C. It is then evaporated, the residue is taken up in 50 ml of water and 50 ml of ethyl acetate, and the aqueous phase is separated off and again evaporated. The substance left is dissolved in a little water and charged onto a column containing 50 ml of Lewatit MP 62 ion exchanger (OH form), which is then eluted with 200 ml of water. The eluate is evaporated in vacuo, leaving a colorless powder, weighing 0.9 g, which represents 50% yield based on 2-phenyl-4-benzyl-oxazolinone-(5); this product sublimes from approx. 230° C. onward.

$C_{10}H_{13}NO_2$ (179.2): found C 66.45; H 7.30; N 7.78; calculated C 67.03; H 7.31; N 7.81.

5. α-benzyl-aspartic acid from 4-(2-phenyl-4-benzyl-oxazolinon-(5)-yl)-acetic acid ethyl ester 2.5 g of 2-phenyl-4-benzyl-oxazolinone-(5), 2.45 g of ethyl chloroacetate, 3.0 g of ethyldiisopropylamine and 0.5 g of potassium iodide in 10 ml of absolute dimethylformamide are stirred for 6 hours at 95° C. The dimethylformamide is then distilled off under reduced pressure and the residue is dissolved in methylene chloride, extracted by shaking with water and again evaporated. The brown oil which remains is stirred with 25 ml of glacial acetic acid and 5 ml of concentrated hydrochloric acid for 8 hours at 90° C. The solution is evaporated in vacuo, the residue is dissolved in a little water/methanol and this solution is neutralized with n-butylamine and buffed to pH 4 with glacial acetic acid. The mixture is again evaporated and the residue is taken up in acetone. On standing overnight, a colorless precipitate forms, and this is filtered off, giving 0.67 g, corresponding to 30% yield, based on 2-phenyl-4-benzyl-oxazolinone-(5). This product is a white powder which decomposes above 275° C.

$C_{11}H_{13}NO_4$ (223.2): found C 59.37; H 6.11; N 6.36; calculated C 59.20; H 5.86; N 6.27.

6. α-isopropyl-3,4-dimethoxyphenylalanine from 4-isopropyl-2-phenyloxazolinone-(5)

2.0 g of 4-isopropyl-2-phenyl-oxazolinone-(5), 1.86 g of 3,4-dimethoxybenzyl chloride, 1.5 g of ethyldiisopropylamine and 0.5 g of potassium iodide in 10 ml of absolute dimethylformamide are stirred for 7 days at room temperature. The mixture is then diluted with 100 ml of water and extracted with five times 20 ml of methylene chloride. The combined extracts are washed with 0.5N hydrochloric acid and with water, then dried with magnesium sulfate and freed from the solvent under reduced pressure. This leaves 3.45 g of a light yellow oil which according to the NMR spectrum contains approx. 65% of the desired product.

This oil is dissolved in 20 ml of glacial acetic acid and 10 ml of concentrated aqueous hydrochloric acid and the solution is stirred for 6 hours at 95° C. It is then evaporated under reduced pressure and the residue is taken up in a mixture of 50 ml of ethyl acetate and 50 ml of water. The aqueous phase is separated off and concentrated to approx. 10 ml. It is then neutralized with n-butylamine and the aminoacid is precipitated by adding methanol/ether and filtered off.

The yield of α-isopropyl-3,4-dimethoxyphenylalanine is 0.4 g, representing 15% based on 4-isopropyl-2-phenyl-oxazolinone-(5) employed. The product is a colorless powder which melts at 260° C.

7. α-methyl-3,4-dimethoxyphenylalanine from 4-methyl-2-phenyl-oxazolinone-(5)

1.75 g of 4-methyl-2-phenyl-2-oxazolinone-(5), 1.86 g of 3,4-dimethoxybenzyl chloride, 1.5 g of ethyldiisopropylamine and 0.3 g of potassium iodide in 10 ml of absolute dimethylformamide are stirred for 4 days at room temperature. The mixture is then diluted with 100 ml of water and extracted with five times 20 ml of methylene chloride. The combined extracts are washed with 0.5N hydrochloric acid and with water, dried with magnesium sulfate and freed from the solvent under reduced pressure. According to the NMR spectrum, the resulting light yellow oil 3.1 g) contains approx. 50% of the desired product. The oil is dissolved in 10 ml of glacial acetic acid, 10 ml of concentrated aqueous hydrochloric acid are added and the mixture is stirred for 7 hours at 95° C. After evaporation under reduced pressure, the residue is taken up in 50 ml of water and 50 ml of carbon tetrachloride, leaving a substantial amount of insoluble resin to be separated off. The water phase is evaporated in vacuo, the residue is dissolved in methanol and the solution is charged onto a column of 50 ml of Levatit MP 62 (OH form). After elution with 100 ml of methanol, the eluate is concentrated and the product is precipitated with ether. Yield 0.35 g, representing 15% based on 4-methyl-2-phenyl-oxazolinone-(5) employed. The product is a white powder which decomposes at about 230° C.

We claim:

1. A process for the manufacture of 2-phenyl-4-methyl-4-benzyl-oxazolinone-(5), which consists essentially of: reacting 2-phenyl-4-benzyl-oxazolinone-(5) with methyl iodide in an anhydrous aprotic solvent in the presence of a tertiary amine selected from the group consisting of triethylamine, ethyldiisopropylamine, a Hunig's base, N,N-dimethyl-cyclohexylamine, pyridine and a picoline at temperatures of from about −10° C. to 100° C.

2. A process for the manufacture of 2-phenyl-4-methyl-4-(3,4-dimethoxybenzyl)-2-oxazolinone-(5), which consists essentially of: reacting 4-methyl-2-phenyl-2-oxazolinone-(5) with 3,4-dimethoxybenzyl chloride in an anhydrous aprotic solvent in the presence of a tertiary amine selected from the group consisting of triethylamine, ethyldiisopropylamine, a Hunig's base, N,N-dimethylcyclohexylamine, pyridine and a picoline at temperatures of from about −10° C. to 100° C.

3. The process of claim 1 or 2, wherein the tertiary amine is ethyldiisopropylamine.

* * * * *